US006439720B1

(12) United States Patent
Graves et al.

(10) Patent No.: US 6,439,720 B1
(45) Date of Patent: Aug. 27, 2002

(54) METHOD AND APPARATUS FOR MEASURING OPTICAL ABERRATIONS OF THE HUMAN EYE

(75) Inventors: J. Elon Graves; Malcolm J. Northcott, both of Kailua, HI (US)

(73) Assignee: Aoptics, Inc., Campbell, CA (US)

( * ) Notice: Subject to any disclaimer, the term of this patent is extended or adjusted under 35 U.S.C. 154(b) by 37 days.

(21) Appl. No.: 09/769,892

(22) Filed: Jan. 25, 2001

Related U.S. Application Data

(60) Provisional application No. 60/178,416, filed on Jan. 27, 2000.

(51) Int. Cl.$^7$ ................................................ A61B 3/10
(52) U.S. Cl. ...................................................... 351/211
(58) Field of Search ................................ 351/211, 212, 351/214, 215, 216, 221, 206, 207

(56) References Cited

U.S. PATENT DOCUMENTS

| | | | |
|---|---|---|---|
| 5,329,322 A | 7/1994 | Yancey | 351/211 |
| 5,576,780 A | 11/1996 | Yancey | 351/211 |
| 5,777,719 A | 7/1998 | Williams et al. | 351/212 |
| 5,949,521 A | 9/1999 | Williams et al. | 351/246 |
| 6,023,057 A | 2/2000 | Gaffard et al. | 250/201.9 |
| 6,331,059 B1 * | 12/2001 | Kudryashov et al. | 351/221 |

OTHER PUBLICATIONS

Laser Guide Star Adaptive Optics Workshop: Proceedings—vol. 1 (Mar. 10–12, 1992).
Publication entitled "A Simple Low–Order Adaptive Optics System For Near–Infrared Applications"; Publications of the Astronomical Society of the Pacific; vol. 103, Jan. 1991, No. 659 by Roddier et al.
Proceedings of SPIE 3353, Mar. 1998 entitled First Light For Hokupa'a; Author Graves et al.
Publication entitled "Objective Measurement of Wave Aberrations of the Human Eye with the Use of a Hartmann–Shack Wave–Front Sensor", J. Opt. Soc. Am. A., vol. 11, No. 7, pp. 1–9, Jul. 1994; Authors Liang et al.
Publication entitled "Scanning Laser Tomography of the Living Human Eye" in Noninvasive Diagnostic Techniques in Ophthalmology. Masters BR (ed.), Springer–Verlag, pp. 528–547 (1990); Authors Bille et al.
Publication entitled "Measurement of the Wage Aberration of the Human Eye"; Biophysics 1961; 6: 776–94; by Smirnov MS.
Publication entitled "Subjective Measurement of High–Order Aberrations of the Eye", Science 1976; 193: 580–2 by Howland B. et al.
Publication entitled "A Subjective Method for the Measurement of Monochromatic Aberrations of the Eye", J. Opt Soc. Am 1977; 67(11): 1508–1518 by Howland HC et al.

(List continued on next page.)

Primary Examiner—George Manuel
(74) Attorney, Agent, or Firm—Lyon & Lyon LLP (57) ABSTRACT

An apparatus for measuring optical aberrations of the human eye wherein the person positions his or her eye on an optical axis of the apparatus and looks at an illuminated target on the optical axis that is visible to the eye for allowing the eye to focus on the target and establish a position of the eye. A collimating lens on the optical axis is movable along the optical axis for adjusting the apparent optical distance between the eye and the target. A light source directs a predetermined light beam along the optical axis into the eye and onto the retina of the eye as a spot of light. A lens reimages the light scattered from the light spot on the eye retina into a wavefront curvature sensor that forms two oppositely defocused images on an image detector, and a computer processes and analyzes the two defocused images for measuring the optical aberrations of the eye.

34 Claims, 4 Drawing Sheets

OTHER PUBLICATIONS

Publication entitled "Objective Technique for the Determination of Monochromatic Aberrations of the Human Eye", J. opt. Soc. Am. A., vol. 1, No. 9, pp. 987–992 (1984) by Walsh et al.

Publication entitled "Measurement of the Axial Wavefront Aberration of the Human Eye". Opthal Physiol Opt. 1985; 5: 23–31 by Walsh, G. et al.

Publication entitled "Wavefront Aberration of the Eye: A Review"; Optometry and Vision Science 1991; 68(3): 574–583 by Charman WN.

Publication entitled "Measurement of Monochromatic Ocular Aberrations of human Eyes as a Function of Accommodation by the Howland Aberroscope Technique"; Vision Res. 1995: 35(3): 313–23 by Atchinson DA et al.

Publication entitled "Reliability and Validity Studies of a New Computer–Assisted Crossed–Cylinder Aberroscope"; Optom Vis. Sci. 1997; 74(7): 570–80 by Cox MJ et al.

Publication entitled "Retrieval of Wave Aberration of Human Eyes from Actual Point–Spread Function Data"; J. Opt Soc. Am 1988; 5(8); 1201–6 by Artal P. et al.

Publication entitled "Wavefront Determination Resulting From Foucault Tests Applied to the Human Eye and Visual Instruments"; In Optical instruments and Techniques, Dickson JH (ed.), London, Oriel, 1969, 375–85.

Publication entitled "Computing High order Wave Aberration Coefficients from Small Variations of Best Focus for Small Artificial Pupils"; Vision Res. 1989; 29(8); 979–83 by Howland HC et al.

Publication entitled "Active Optical Depth Resolution Improvement of the Laser Tomographic Scanner"; Applied Optics, vol. 28, No 4, pp. 804–808, (1989) by Dreher et al.

Publication entitled "Curvature Sensing and Compensation: A New concept in Adaptive Optics"; applied Optics, vol. 27, pp. 1223–1225, 1988 by Roddier F.

Publication entitled "Wavefront Sensing and the Irradiance Transport Equation"; Applied Optics, vol. 29 (10), pp. 1402–1403, 1990 by Roddier F.

Publication entitled "New Optical Testing methods Developed at the University of Hawaii; Results of Ground–Based Telescopes and Hubble Space Telescope"; SPIE, vol. 1531. pp. 37–43, 1991 by Roddier C. et al.

* cited by examiner

METHOD AND APPARATUS FOR MEASURING OPTICAL ABERRATIONS OF THE HUMAN EYE

This application basis priority on Provisional Patent Application Serial No. 60/178,416, filed Jan. 27, 2000.

FIELD OF THE INVENTION

The present invention relates to methods and optical instrumentation for objectively measuring the aberrations of the human eye and specifically to an instrument capable of measuring not only the focus (spherical) and astigmatism (cylindrical) characteristics and aberrations of a person's eye but also all of the lower and higher order optical aberrations that are derived from a measured wavefront utilizing a wavefront curvature sensor.

BACKGROUND OF THE INVENTION

Measuring the aberrations of an optical system, including a human eye, is an important part of working with any optical system. Existing methods of measurement include various interferometric techniques, the Shack-Hartman wavefront sensor, and various systems involving the projection of patterns through the optical system. These systems are typically complex and expensive and most require access to the focal plane.

The human eye, although comprised of only a few optical components, may manifest a wide variety of optical aberrations that vary from person to person and over time. These aberrations may result from surface contour shape, lens thickness factors, axial alignment of refractive surfaces, axial length of the eye, and even localized refractive index variations. The fact that the human eye possesses optical aberrations has been known for centuries. Nevertheless, the measurement and characterization of these aberrations, primarily the monochromatic aberrations, has remained a problem and has fostered much research in physiological optics over the years. Finding the proper prescription, even in modern times, has been primarily based on the subjective responses to the viewing of eye charts by the person being tested, whereas recent advances in corrective methods have emphasized objective measurement of these aberrations.

Current methods of optical correction of the human eye to allow clear vision include spectacles, contact and intraocular lenses, and refractive surgery. Spectacles, the most commonly used method, only allow correction of sphere (defocus) and regular or symmetric cylinder (astigmatism). None of the present methods allow for correction of other aberrations and thus do not maximize the optical potential of the visual system, leaving the images generated to be less than optimal. In addition, not only is the view out of the eye not optimal but so is the view in. Thus, the examination of the eye's interior is also limited by these aberrations, and in some clinical situations, is severely handicapped.

Recently, great interest in this area has been kindled by the development of laser technologies, such as the excimer laser, whereby the refractive or optical errors of the eye, such as myopia (nearsightedness), hyperopia (farsightedness) and astigmatism, can be corrected by laser abelation or sculpting of the cornea. Such treatment creates a new corneal contour, or curvature, designed such that the image becomes clearly focused on the retina of the eye. Many degrees of myopia and hyperopia, with or without astigmatism, and astigmatism alone can now be corrected by such laser corneal surgery.

Although the clinical results of such surgery are good, it has been postulated, on the basis of experiment, that improved results could be obtained if the surgery were customized fully to correct all the optical aberrations of the eye, not just the sphere and cylinder. Super vision at the diffraction limit set by the aperture is possible. This could be accomplished by a computer-directed small spot scanning laser and sophisticated algorithm that takes into consideration all the aberrations of the eye. Also, many subject's have irregularly shaped corneas, not currently treatable. In addition, the asphericity of the modified cornea is often significantly increased. Clinical studies have indicated that current autorefractors, when used to determine the refraction, or optical prescription, of surgically modified eyes may provide less reliable data in such cases. Even in normal eyes, their accuracy is such that the information cannot be routinely relied upon but must be verified by further subjective testing.

It is apparent that a complete diagnosis and understanding of the eye's optical function, as the organic optical instrument, is currently very limited. A full evaluation should provide a complete description of the optical characteristics and aberrations in a quantitative format. Only then can there arise the possibility of correcting the abnormalities.

Theoretically, light arriving at the eye from a point source at infinity arrives in the form of a plane (flat) wave, whereas light from closer objects provide a wave with a convex spherical shape. This wave, in an ideal eye, would be focused as a discrete point limited only by diffraction on the retina of the eye. However, because of the optical aberrations of the eye, a degraded or blurred image is created on the retina. This concept can be appreciated in the reverse direction with resultant utility.

A plane wave, directed into the eye, would form a spot on the retina. In reverse this spot scatters light which escapes through the same optical path from which it came in. Because this light originates from a scattering process the incoming wavefront information is lost, resulting in a new source which originates from the back of the eye. This emergent wavefront now processes only the aberrations of the eye on a single pass. The present inventors have discovered that the distorted shape of this source, caused by incoming aberrations, can uniquely be eliminated with the differential curvature wavefront sensing method. Measurement and characterization of this wavefront allows one to describe the aberrations of the eye mathematically. Presently, some of these concepts are taken advantage of in ground-based telescope systems that are typically coupled with adaptive optical elements in a closed loop system. They can rapidly neutralize the wavefront aberrations induced by atmospheric turbulence and produce images that are limited only by diffraction and the aperture of the telescope.

Unfortunately, current subjective clinical methodology and instrumentation, such as the phoropter and objective devices such as autorefractors, do not avail themselves of this understanding and are based on concepts and techniques that restrict measurements to defocus and astigmatism only. During the past decade, this limitation has been appreciated and devices called corneal topographers, utilizing images reflected by the cornea, have been developed to obtain more optical information about the eye. However, they gather optical information about only one surface in the eye's refractive system and reveal nothing about the system as a whole.

A number of investigators have attempted or suggested means whereby the wavefront, either explicitly or implicitly, was recognized as an entity to be captured and determined.

These studies were interested primarily in determining the monochromatic aberrations of the eye rather than the development of autorefractor-like devices for routine clinical use or methods of correction.

A number of approaches have been taken to measure the monochromatic aberrations of the eye. Some used projecting rays or patterns of light into the eye and analysis of the images by subjective or objective means. Initially this work, such as present by M. S. Smirnov ("Measurement of the Wave Aberration of the Human Eye", Biophysics, 1961; 6:776–94) was carried out using subjective sequential subject testing, which was inaccurate and time consuming. More studies, however, have been performed using a modification of the principle first presented by Tscherning in 1894. One approach employed a device called the crossed cylinder aberroscope (Howland B and Howland H C: Subjective measurement of high-order aberrations of the eye. Science 1976; 193:580–02 and Howland H C and Howland B: "A subjective method for the measurement of monochromatic aberrations of the eye", J. Opt Soc. Am 1977; 67(11): 1508–1518). Initially, this device was used in a subjective fashion whereby a drawing was made of an object by the test subject and later analyzed mathematically by computer to calculate the wavefront. This allowed for the mathematical characterization of the wavefront in mathematical terms, such as a Taylor series expansion or Zernike polynomials, and it was determined that the aberrations were dominated by third-order Taylor terms. Later, this method was converted to an objective approach by Walsh et al.

In the objective aberroscope method a point source of light is viewed through a grid placed close to the eye (Walsh et al., "Objective Technique for the Determination of Monochromatic Aberrations of the Human Eye", J. Opt. Soc. Am. A., 1984; Vol. 1, No. 9, pp. 987–992 and Walsh G, Chairman W N: "Measurement of the axial wavefront aberration of the human eye", Opthal Physiol Opt, 1985, 5:23–31). This results in an aberrated image of the grid on the retina that can be photographed and analyzed by ray tracing. Although multiple points at the grid line intersections can be captured at the same time, it has been found that diffraction effects prevent sampling the papillary area at intervals much less than 1 mm which limit the determination of fine detail (Chairman W N: "Wavefront Aberration of the Eye: A Review", Optometry and Vision Science 1991; 68(3): 574–583). Other drawbacks were the lack of a rapid means of analysis and the faulty assumption that the aberrations could be characterized by terms of only up to the fourth order. The former problem has been improved upon with more computerized versions (Atchinson D A, Collins M J, Wildsoet C F, Christensen J. Waterworth M D: "Measurement of monochromatic ocular aberrations of human eyes as a function of accommodation by the Howland aberroscope technique", Vision Res 1995; 35(3): 313–23 and Cox M J and Walsh G: "Reliability and validity studies of a new computer-assisted crossed-cylinder aberroscope", Optom Vis Sci 1997; 74 (7): 570–80).

Several investigators attempted other objective methods, whereby the wavefront was determined from the point-spread function data using a hybrid optical-digital instrument (Artal P, Santamarfa J. Bescos J: "Retrieval of wave aberration of human eyes from actual point-spread-function data", J Opt Soc Am 1988; 5(8); 1201–6).

Another objective approach was based on a modified Foucault knife-edge method as a double-pass ophthalmoscopic method and allowed wavefront aberrations to be inferred from two flash photographs obtained with the knife-edge oriented in orthogonal directions. This demonstrated significant irregular components (Berny F and Slansky S: "Wavefront determination resulting from Foucault tests applied to the human eye and visual instruments", Optical Instruments and techniques, Dickson J H (ed), London, Oriel, 1969, 375–85).

Howland used an approach whereby variations of focus across the natural pupil by employing a small artificial pupil and a telescope with an adjustable focus, and related the measured variations in focus to wave aberrations of the eye (Howland H C and Buettner J: "Computing high order wave aberration coefficients from small variations of best focus for small artificial pupils", Vision Res 1989; 29(8): 979–83).

The most recent direction taken in the measurement and correction of monochromatic aberrations of the eye involves the technologies of adaptive optics or deformable mirrors and wavefront sensors. The use of a deformable mirror has been proposed to assist in the neutralization of the wavefront error to improve the function of a confocal laser scanning ophthalmoscope for use with the human eye, and the method was to correct the low order aberration of astigmatism (Bille U.S. Pat. 4,838,679 and Dreher, Bille, and Weinreb, "Active optical depth resolution improvement of the laser tomographic scanner", Applied Optics, 1989 Vol. 28, No. 4, pp. 804–808). In neither case, however, was a specific method to measure the aberrations developed or disclosed.

Others used a Hartmann-Shack wavefront sensor, developed and used in astronomy in conjunction with adaptive optics to neutralize atmospheric turbulence, to measure the eye's aberrations (Williams et al. U.S. Pat. No. 5,777,719 and Liang, et al., "Objective measurement of wave aberrations of the human eye with the use of a Hartmann-Shack wave-front sensor", J. Opt. Soc. Am. A., July 1994 Vol. 11, No. 7, pp. 1–9). The sensor is an array of multiple lenslets, constructed of two identical layers of cylinders set 90 degrees apart that act as an array of spherical lenslets. The reflection of a beam of light incident onto the fovea is imaged by the lenslet array and analyzed by computer, deriving the wavefront emergent from the eye. An acknowledged limitation of the system was that only polynomials up to the fourth degree were used to represent the wavefront, which is considered inadequate (Williams U.S. Pat No. 5,777,719). Bille also proposed the combination of a wavefront sensor and an adaptive optical element but the details have never been disclosed (Bille et al.; "Scanning laser tomography of the living human eye"; Noninvasive Diagnostic Techniques in Ophthalmology. Masters B R (ed), Springer-Verlag, 1990, pp. 528–47).

The first detailed description of a device that combined both a wavefront sensor and an adaptive optical element was disclosed by Williams, et al. U.S. Pat No. 5,777,719. The proposed instrument was primarily a retinal fundus imaging device that used the Hartmann-Shack wavefront sensor as the basis of obtaining the wavefront. The wavefront is expressed in terms of Zernike polynomials, which are then used to appropriately deform a mirror such that the eye's aberrations could be neutralized or compensated for to provide high resolution retinal imaging or to provide supernormal vision while viewing with the assistance of the device. Disadvantages with this technique are the complexity, construction and cost of the Hartman-Shack wavefront sensor. Also, depending upon the magnitude of the aberrations, significant deviations of the wavefront at certain locations could be erroneously ascribed to the nearest lenslet whereas the signal arose from a location further away. In addition, the deformable mirror described is extremely complex and costly to construct. Although perhaps capable of determining and neutralizing the wavefront, the design does not describe how the device could be used as a common tool in clinical practice to determine the refraction of the eye in an economical way.

Another approach, called curvature wavefront sensing, is an old qualitative technique, which the present inventors have discovered can be made quantitative, with the aid of new technology and modern computers, for examining the human eye. It is inexpensive to implement and can determine a wide range or aberrations through a large tunable dynamic range. Curvature wavefront sensing has been employed in closed-loop adaptive optics systems in astronomy by one group for some years and has been reported on several publications where the optical principles involved are described (Roddier F: Curvature Sensing and Compensation: "A new concept in adaptive optics", Applied Optics, 1988, Vol. 27, pp. 1223–5; Roddier F: "Wavefront Sensing and the Irradiance Transport Equation. Applied Optics, 1990, Vol. 29 (10), pp. 1402–3; and Roddier C and Roddier F: "New Optical Testing Methods Developed at the University of Hawaii: Results of ground-based Telescopes and Hubble Space Telescope". SPIE, 1991, Vol. 1531, pp.37–3), which publications are incorporated herein by this reference for explanatory background.

SUMMARY AND OBJECTS OF THE INVENTION

It is a primary object of the present invention to provide both a method and an apparatus for accurately and quickly measuring the optical aberrations of the eye, including focus, astigmatism and higher order aberrations.

It is another object of the present invention to provide such an apparatus with a wavefront curvature sensor with the capability of measuring the optical aberrations of the eye.

It is a further object of the present invention to provide methods and apparatus for obtaining defocused pupil images that make diffractive effects symmetrical, and thus maximizes the accuracy of the wavefront sensor and the analysis of the aberrations of the human eye.

It is a still further object of the present invention to provide a method and apparatus for obtaining defocused images at high speed, thus allowing the information to be used for real time correction of the optical aberrations by several means.

Still a further object of the present invention is to provide a method and apparatus for tuning the dynamic range of the measurements taken with the wavefront sensor to suit the wavefront under consideration.

A still further object of the present invention is to provide a method and apparatus for minimizing strong images caused by the reflection from the ocular refracting surfaces of the eye in the measurement beam.

It is still another and further object of the present invention to provide a method and apparatus for measuring the pupil size and shape at the time of the wavefront measurement.

Other and more detailed objects and advantages of the present invention will appear to those skilled in the art from the following detailed description of the preferred embodiments in conjunction with the drawings.

DETAILED DESCRIPTION OF THE PREFERRED EMBODIMENT AND VARIATIONS

Figures 1, 2:
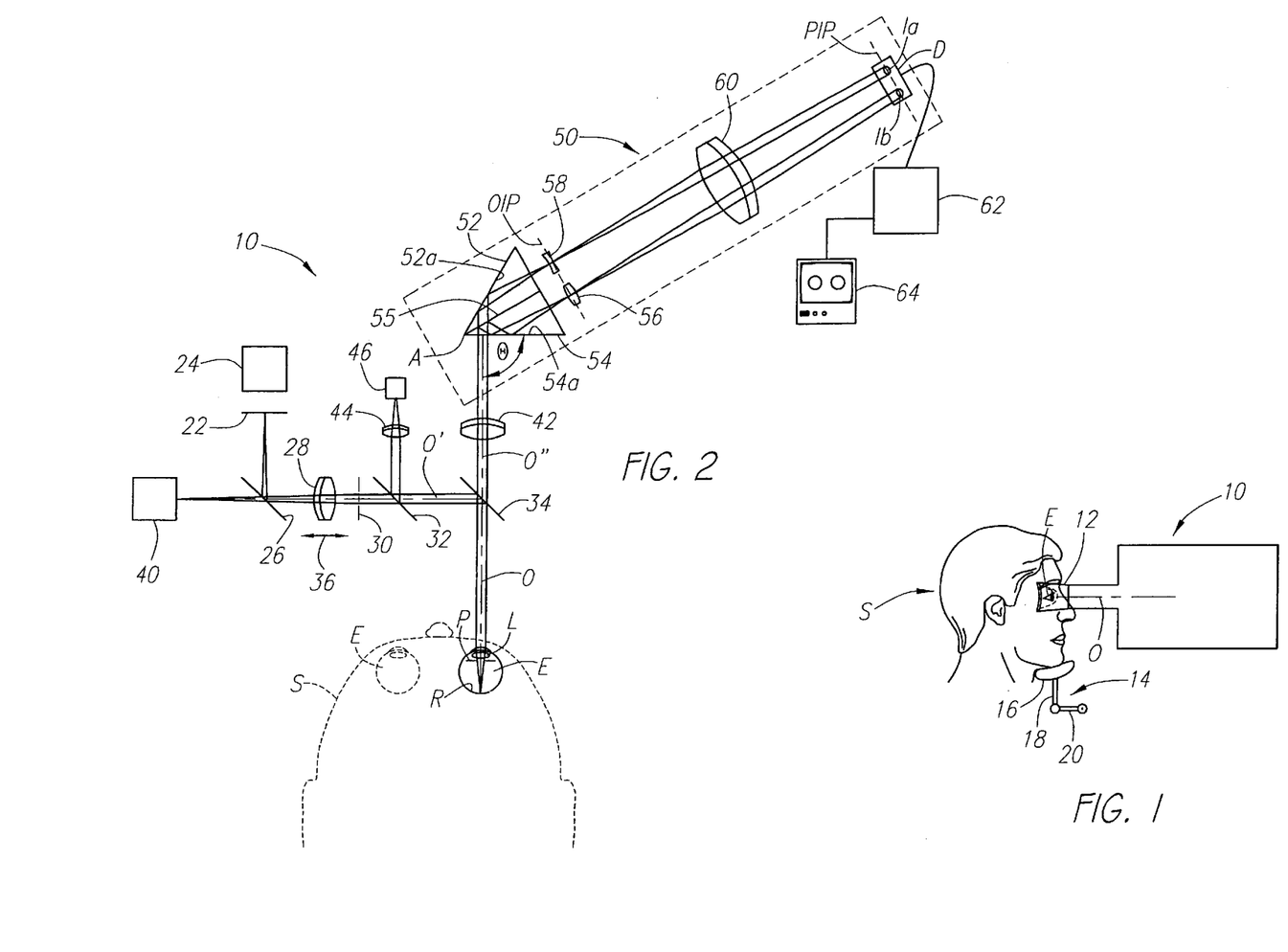
FIG. 1 is a diagrammatic side elevation view of a person using the apparatus of the present invention.
FIG. 2 is a diagrammatic plan view of the optical system of a preferred embodiment of the apparatus of the present invention.

Referring now to FIGS. 1 and 2, the subject person S that is to have his or her eyes analyzed by the optical apparatus, generally designated 10, of the present invention positions one eye against a flexible eye cup 12 for aligning the center of the pupil of that eye with the optical axis O of the apparatus 10. Preferably, the head of the subject person S is adjusted to obtain that alignment and then supported in that position by any convenient means, such as an adjustable chin support 14. For example, a shaped pad 16 may be supported by a pair of pivotally connected links 18 and 20 that can be manipulated and then locked in position when the subject person S has his or her eye E in appropriate alignment with the optical axis O, which alignment can be determined by the operator of the apparatus in a manner described below. For clarity of illustration, the eye cup 12 is omitted from the schematic plan view FIG. 2.

Referring more particularly to FIG. 2, the optical apparatus 10 is provided with a target 22 that is preferably back-lighted by an illuminator 24 to be visible by the subject person S having an eye E looking into the apparatus. The target 22 may be of any shape or representation that encourages the subject person S to focus his or her eye E on an exact point for inhibiting movement of the eye E during the measuring and analyzing steps performed by the apparatus 10, such as a target with gun sight type crosshairs, concentric circles, a pattern, a scene or the like. The light from target 22 is reflected by the partial mirror or beam splitter 26 along optical axis portion O' through a collimating lens 28, a mask 30 and another partial mirror or beam splitter 32 to a polarizing beam splitter 34 which reflects the light from the target 22 into the eye E of the subject person S along the main portion of the optical axis O. The collimating lens 28 preferably is adjustably movable along the optical axis O', as shown by the double arrow 36 to adjust the apparent image distance of the accommodation target 22 from the eye E for optimizing the ability of the eye E to focus on the target 22. Thus, the person S views with the eye E an incoherently back-illuminated accommodation target 22 during use of the optical apparatus 10 for establishing a fixed location, orientation and focus adjustment of the human eye E to the maximum extent possible without physically contacting the eye E during operation of the optical apparatus 10.

A probe beam of light originating from any appropriate light source 40, such as a laser diode, or any other bright polarized or non-polarized point source of light, is directed along the optical axis O' through the beam splitter 26 where it combines with the light from accommodation target 22 and then through the collimating lens 28, mask 30 and beam splitter 32 to reflect from the beam splitter 34 along the main optical axis O into the eye E. Preferably, the light from light source 40 is of a wavelength that is readily detected by the type of detectors, described more fully below, used in the optical apparatus 10, such as silicon detectors, but of a wavelength that is safe and relatively invisible to the retina R of the eye E. Red light is particularly suited for this apparatus because the red light is not absorbed by the eye retina, as is blue and yellow light. The light is scattered by the retina R and emerges through the pupil P.

Figure 3:
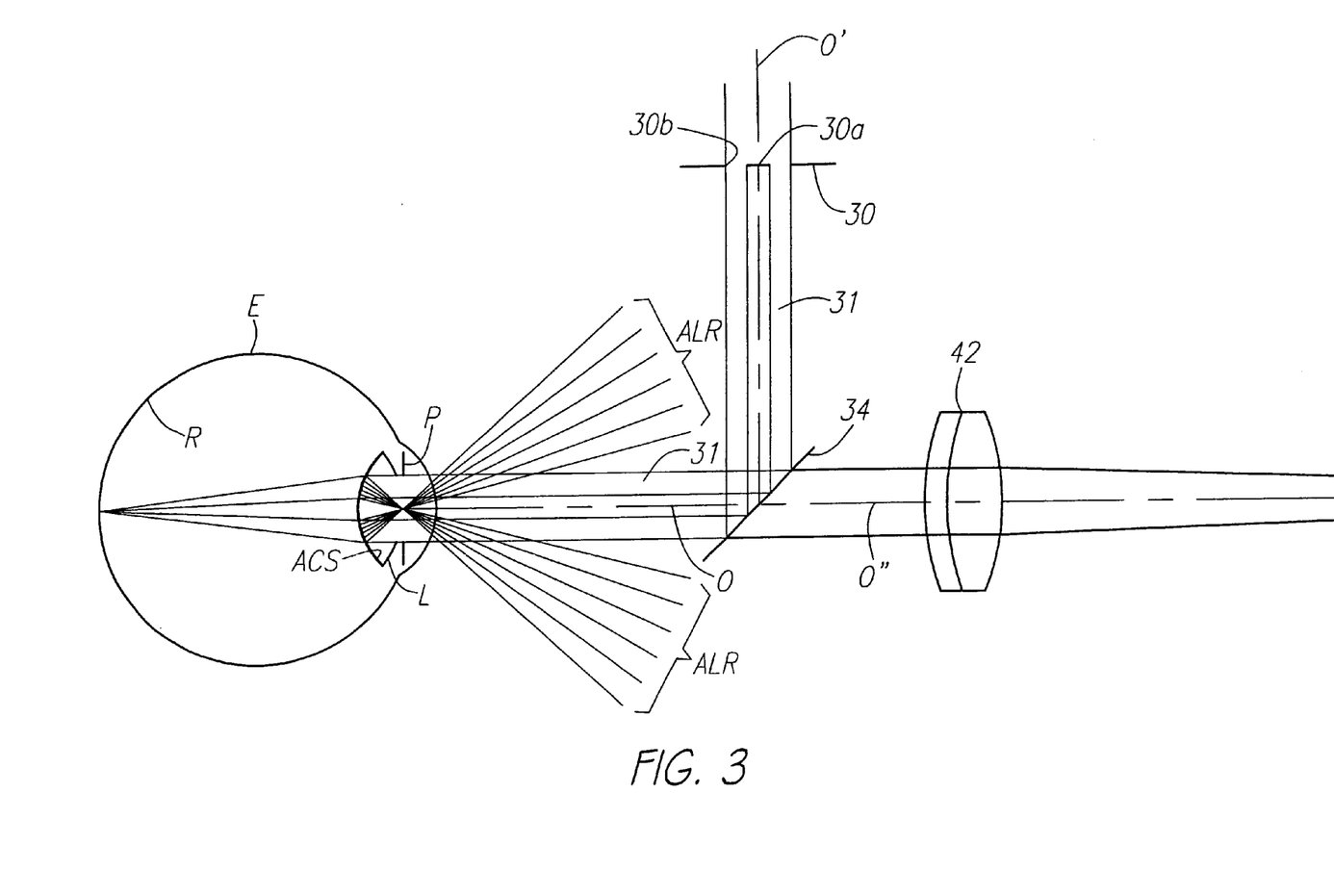
FIG. 3 is a simplified optical diagram of a portion of the system of FIG. 2 for describing the light reflections and scattering by the human eye using the light source of the apparatus of this invention.

Referring now to FIG. 3, which is a simplified optical diagram of a portion of the system of FIG. 2, the light beam from light source 40 (not shown) is directed along optical axis O' and passes through mask 30 to polarizing beam splitter 34 where it is reflected toward eye E along optical axis O. The mask 30 is comprised of a circular pupil stop opening having an opaque central obscuration 30a and a surrounding circulars opening 30b to thereby form a donut-shaped annular ring of light beam 31 from source 40. The mask 30 may be in the form of a glass plate with the masking material applied thereto. The annular light beam 31 enters the eye E and is focused on the retina R as a small spot of light that is then scattered before emerging from the eye E as a circular (non-annular) light beam along optical axis O. Since the retina scatters the light, the emerging light is not polarized and therefore passes through the polarized beam splitter 34 and then along optical axis O" to lens 42. However, not all of the light returning from the eye E comes from the retina R and can cause problems in measuring an accurate wavefront. Some of the light projected toward the eye E is reflected by specular reflection from the eye's optical surfaces, but predominantly this light is reflected from the anterior crystalline surface ACS. Being a concave surface this light is reflected back out the eye in a converging beam whose focal point is located on the iris. This is a design feature of the eye which assures that all the light reflected from this surface will exit the eye and not be scatter off the back of the iris. Since the annular light beam 31 impinges only on an annular portion of the anterior crystalline surface ACS, the reflected light is an annular beam of light rays ALR that expands after passing through the pupil P, with no light in the center, whereby the light rays ALR can not reach lens 42. As this annular beam ALR exits the eye it is expanding at the focal ratio at or near f/1. The central obstruction 30a of the mask is adjusted to a f/ which is faster than that of the wavefront sensor optics. This arrange effectively removes this reflected light from the system. The small amount of light reflecting off other surfaces in the eye which are not removed by the method described above is partially removed with polarization. Light returning along the optical axis by reflection, at near normal incidence maintains its polarization and, therefore, is directed back to the source 40 by the beam splitter 34 and not into lens 42 and the wavefront sensor 50.

The portion of light from the annular light beam 31 that passes through the eye lens L is focused on the retina as a small spot. Adjustments to lens 36 are made by the patient to sharpen the image of the target 22 whereby the light spot on the retina is small and focused. The light rays from that light spot are scattered by the retina R so the light is non-polarized and therefore half of such light passes through the polarized beam splitter 34 to the collimating lens 42 and then to the wavefront sensor 50. The target 22 and light source 40 are conjugate. The manner in which that light is analyzed by the wavefront sensor 50 will be described below.

Although it is not absolutely essential to the herein disclosed apparatus and method for measuring the optical aberrations of the human eye, it is desirable and the aberration measurement accuracy can be improved by recording the geometry of the pupil P of the human eye E at the exact moment that the defocused pupil images are being recorded by the wavefront sensor 50. This is because not all human eye pupils P are exactly round and any deviation from round can introduce errors in the wavefront calculations because such calculations initially are based on the assumption that the pupil is round and are not modified unless a different shape is determined. In addition, unless immobilized with drugs, the average pupil is constantly changing size with time, its exact size at the moment the defocused images are recorded is needed to improve the measurement accuracy. Further, by dilating the eye E, the maximum amount of eye lens L can be analyzed. In the apparatus 10 the pupil geometry is obtained and recorded with a suitable camera 46. The iris can be illuminated by any suitable light source which will return light along the optical axis O to beam splitter 34 where the light is reflected along optical axis portion O' to the beam splitter 32 where a portion of the light is reflected to and through a lens 44 and then to a suitable camera 46 which records the exact shape of the pupil P of this eye E of the subject person S. By providing the camera 46 with a monitor, the sharpness of the pupil image may be checked by the operator and appropriate adjustments made, such as by adjusting lens 46 or moving person's head. The capturing of the pupil image is synchronized by the computer 62, described below, with the capturing of the images by the wavefront sensor 50 to thereby enhance the measurements of the aberrations.

The wavefront sensor 50 of the optical apparatus 10 may be of any convenient type that provides an accurate measurement and record of the defocused pupil images in either visible or invisible light rays scattered from the retina R of eye E along the axes O, O' to the wavefront sensor 50. It is preferred that the wavefront sensor is of the type that obtains two defocused or extra-focal images of the pupil P, such as disclosed in the copending U.S. patent application Ser. No. 09/579,786, filed May 26, 2000 by the inventors hereof and entitled "Method And Apparatus For Wavefront Sensing", which is incorporated herein by this reference. To avoid any inaccuracies that may result from changes in the human eye E over a few moments time, it is preferred that the two defocused images be obtained simultaneously. One of the embodiments disclosed in our aforesaid copending patent application that simultaneously obtains such defocused images, whereby it is well suited for the optical apparatus 10, is shown in FIG. 2 for illustrative purposes but the present invention is not limited to that embodiment of the wavefront sensor.

Any light rays scattered from the retina R of the eye E that exit the eye, carry information about any aberrations that exist in the crystalline lens and cornea of the eye, which in turn produce variations in the wavefront that are sensed by the wavefront sensor 50 that measures those aberrations to then permit, for example, the creation of corrective eyeglass lenses, contact lenses, inner ocular lenses or laser corrective surgery. The light rays from the eye E that pass through the polarized beam splitter 34 are received by the lens 42 and focused at two separate locations on an object image plane OIP through a pair of Littrow prisms 52 and 54 that are mounted back to back in the Köster configuration in the wavefront sensor 50. A partial mirror or beam splitter 55 is provided at the abutting surfaces of the two Littrow prisms 52, 54 which may be in the form of a thin glass plate beam splitter or a coating on one of the abutting surfaces of the prism to split the incoming light rays evenly (50—50), that is, to cause one-half of the light to pass through the beam splitter 55 to the prism 52 and cause the other one-half of the light to reflect from the beam splitter 55 back into the prism 54. The light passing through the beam splitter 55 reflects off the interior surface 52a of prism 52 to a negatively powered analyzer lens 58 located in the object image plane OIP. The light reflected off the beam splitter 55 then reflects off of the inside of surface 54a of prism 54 to a positively powered analyzer lens 56 located in the object image plane OIP. Thus, the Littrow prisms 52, 54 of the wavefront sensor 50 create two optical axes along which the light from the same light source simultaneously passes through the analyzer lenses 56 and 58 to a collimating lens 60 and then to a pupil image plane PIP on a detector D. Preferably, the Littrow prisms 52 and 54 are slightly titled with respect to each other from their apexes A or, as an alternative, the two Littrow prisms 52, 54 are tilted together about the apex A to create an angle θ between the optical axis O" and surface 54a of slightly less than or more than 90° whereby, in either case, the optical axes of the two light beams emerging from analyzer lenses 56, 58 are not precisely parallel and therefore two pupil images Ia and Ib are separately formed on the detector D. The spacing of the collimating lens 60 and detector D from the object image plane OIP are such that without the analyzer lenses 56 and 58 the pupil images Ia and Ib will be in focus on the pupil image plane PIP of detector D but, if not, the position of lens 60 may be adjusted. However, the analyzer lenses 56 and 58 create two defocused pupil images on the detector and, preferably, the optical powers of the negative analyzer lens 58 and positive analyzer lens 56 are equal but opposite whereby the pupil images Ia and Ib are equally but oppositely defocused and therefore the analysis of those images is simplified. The optical powers of the analyzer lenses 56, 58 may be varied for increasing or decreasing the sensitivity of the wavefront sensor 50.

The detector D of the wavefront sensor 50 may be of any convenient type that is particularly suited for this application of sensing the pupil image of the pupil P of a human eye E. For example, the detector D may be a conventional detector of the type found in a video camera, a custom format of charge couple devices (CCD), an array of PIN diodes, an array of lenslets focusing the light onto an array of optical fibers, photon detectors, etc. that will provide images and/or data relative to the light intensity throughout the defocused pupil images.

The two defocused pupil images Ia and Ib (or the shapes and light intensities for some types of detectors D) are communicated to a computer 62 and, simultaneously, the focused pupil image recorded by camera 46 is communicated to the computer 62, which images may be displayed selectively on the video monitor 64 for observation by the operator. The two defocused images Ia and Ib are processed by data reduction software in the computer 62 to derive the wavefront and provide data appropriate for the measurement of the aberrations of the human eye E. Here, it is preferred to use a CCD or similarly imaging detector for detecting the light intensities. After the normal gradient of the wavefront at the boundaries of the pupil are found, the difference in intensities between the two extra-focal or defocused pupil images Ia and Ib is proportional to the curvature of the wavefront at points inside the pupil image. The wavefront is derived or recovered by solving the Poisson equation with respect to intensities with Dirichlet's boundary conditions relative to shape. An iterative data reduction algorithm or other non-linear fitting technique may be employed to compensate for non-linearity in the measurements. The wavefront obtained may be expressed in orthogonal functions, such as Zernike polynomials, the terms of which provide values of the optical aberrations of the eye, including focus, astigmatism and higher order terms. The full complex wavefront that may be obtained from the data developed by the wavefront sensor includes the wavefront phase and amplitude. The wavefront phase provides complete information relative to what is conventionally thought of as the optical aberrations and the wavefront amplitude provides information relative to inclusion opacities or other optical throughput problems in the subject's eye.

In the normal operation of the optical apparatus 10, the operator is involved in both the setup procedure and the post-examination evaluation at a series of measurements to assess the data quality. Preferably, the probe beam from light source 40 is strobed to effectively act as a shutter to produce separate and distinct images at the camera 46 and detector D during the eye examination. Reliable and very fast shutter speeds are capable with laser diode technology. The light source 40 and accommodation target 22 are conjugate for the proper set up, when the operator has properly aligned the eye E and head of the subject S in the optical apparatus 10, as shown in FIGS. 1 and 2, and the subject person is properly focusing and fixating on the accommodation target 22, the patient sees the sharpest image of the target and this. creates the smallest image of the light source on the retina for improving the analysis. The smaller spot on the retina the better. Small wavefront detail structures and wavefront sensor sensitivity are both related to the size of this image. Another setup task is to assure that there is a sharp image of the pupil on camera 46. If it is fuzzy, then the patient's head must be moved either forward or backwards to bring it into focus. An alternate method would be to move lens 44 and simultaneously move lens 60. A sharp image of the pupil on the detector when the analyzer lenses 56 and 58 are removed is very important. The probe beam is briefly flashed to freeze any motion for evaluating the set up and collecting test data. Each measurement cycle of an exposure and the computation takes only a few seconds thereby making it very easy to take a series of measurements. Post inspection of both the raw and processed data is useful to determine the quality of the measurement. Problems which can occur fall into a number of categories, such as, (1) did the patient move during the procedure, (2) did the patient blink, (3) did the patient stop looking at the desired place on the target, (4) was the pupil in good focus, etc. Inspection of the pupil image lets the operator know about items 1, 2 and 4 but not item 3. Inspection of the defocused images lets the operator know about item 3 and to a lesser degree items 1 and 2. The operator may check the quality of the data or, as an alternative, the computer 62 may be programmed to check the data quality or to automatically make this determination. The subject person may wear spectacles or contact lenses during this examination procedure, resulting in the measurement of the residual aberrations after normal optical correction. By doing so, only a small adjustment of lens 44 and lens 60 is then needed to account for the apparent shift in pupil distance relative to the optical elements in the apparatus 10.

Figure 4:
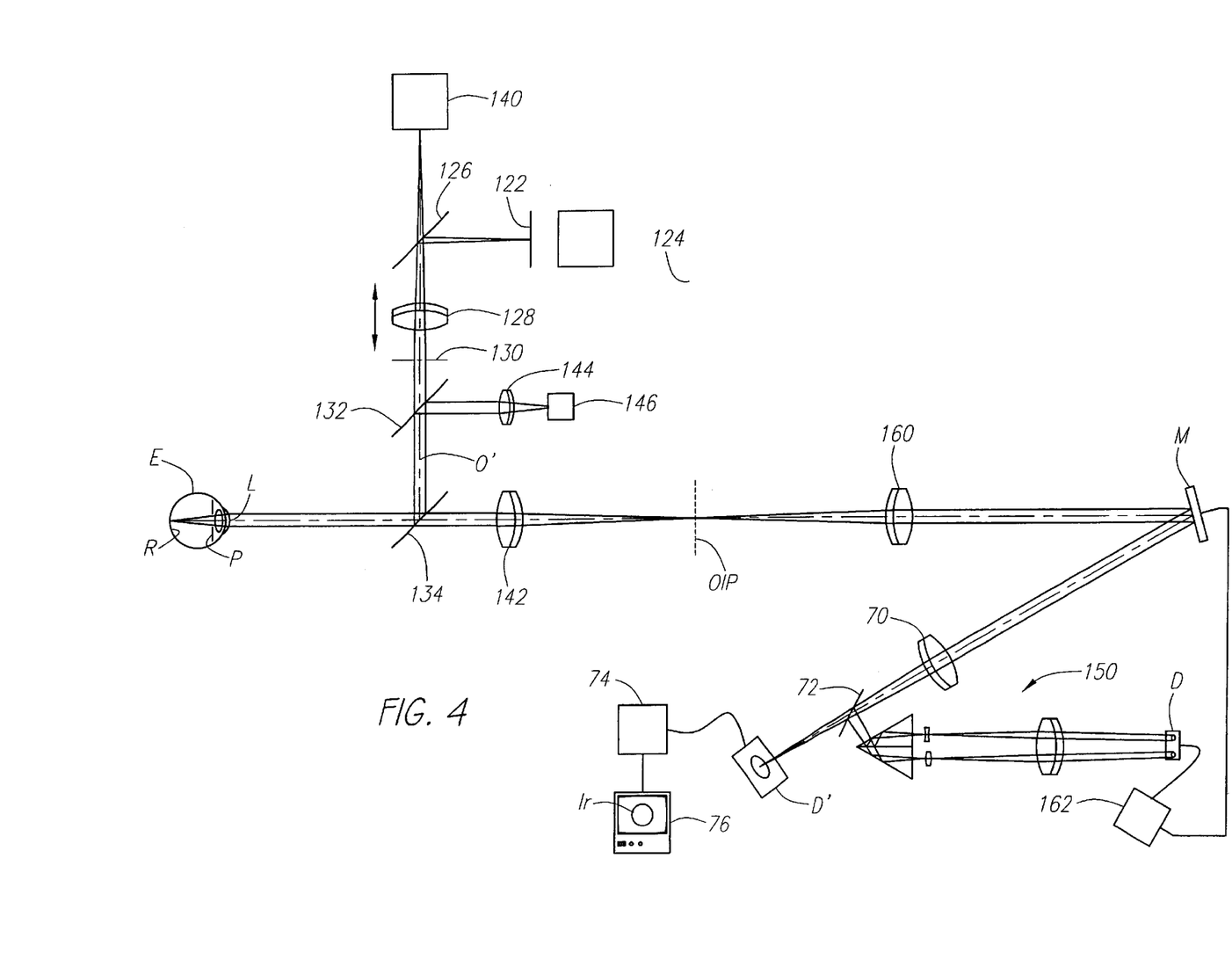
FIG. 4 is a diagrammatic view of a modified embodiment of the optical system illustrated in FIG. 2 with adaptive optics elements and features.

Referring now to FIG. 4, a simplified optical diagram of a modified optical apparatus 110 is diagrammatically illustrated for describing the manner in which adaptive optics may be used in the present invention of a method and apparatus for measuring the optical aberrations of the human eye. Some of the components of the optical apparatus 10 illustrated in FIG. 2 have been omitted from FIG. 4 for simplicity and others have been relocated for accommodating the adaptive optics aspect of the system. The components of optical apparatus 110 in FIG. 4 that are identical to the components of optical apparatus 10 in FIG. 2 will be identified by the same numeral in the one hundred series, such as light source 140 in FIG. 4 being the same as light source 40 in FIG. 2, and therefore a detailed description of those components will not be repeated here with respect to FIG. 4. Again, a controlled light beam emitted from light source 140, such as a laser diode, is projected along an optical axis O' through a collimating lens 128 to a polarized beam splitter 134 where the light is reflected along optical axis O into the human eye E where some of the light is reflected by a specular reflection from the eye's optical surfaces and some of the light passes through the eye lens L and pupil P to the retina R where it is focused as a spot of light and scattered back through the pupil P and eye lens L along optical axis O. The scattered light from the retina R passes through the polarizing beam splitter 134 along optical axis 0" to a lens 142 which focuses the spot of light from the retina on an optical image plane OIP. The light rays continue uncorrected to a collimating lens 160 from which the light rays are directed to a deformable mirror M positioned at a small angle to the collimated light. The light is reflected from deformable mirror M along another optical axis portion 0'" through a lens 70 to a beam splitter 72. Some of the light passes through beam splitter 72 and is focused on a detector D' while the balance of the light is reflected from the beam splitter 72 into a wavefront sensor 150. The detector D' is connected to a computer 74 which in turn is connected to a video monitor 76 on which the retina image is sensed by the detector D' may be displayed. As with the optical apparatus 10 of FIG. 2, the wavefront sensor 150 is connected to a computer 162 which processes and analyzes the two defocused pupil images provided by the scattered light from the spot of light on the retina R of the eye E. The computers 162 and 74 may be combined.

In the adaptive optics system of FIG. 3, the computer 162 is operatively connected to the deformable mirror M, which may be of any convenient type that is capable of controlled deformation for correcting the curvature of the wavefront. A preferred form of such a deformable mirror M is disclosed in the concurrently filed copending U.S. patent application Ser. No. filed 09/769,988, filed Jan. 25, 2001 by the inventors hereof and entitled "Deformable Curvature Mirror", which is incorporated herein by this reference. As disclosed more fully in that copending application, a plurality of wires (not shown) are electrically connected to a like plurality of electrode segments (not shown) on the back of the deformable mirror M and by separately applying and controlling a high voltage applied to each wire by the computer 162, the curvature of the reflective front surface of the deformable mirror M may be controlled.

In using the adaptive optics system of FIG. 4, the deformable mirror M is initially set at a completely flat condition and the light scattered from the spot of light on the retina R proceeds through the apparatus in the manner described above to form an image on the detector D' that may be viewed on the monitor 76 as the uncorrected retina image Ir. Simultaneously, the uncorrected pupil image is supplied by beam splitter 72 to the wavefront sensor 150 wherein two defocused pupil images are formed on a detector D and supplied to the computer 162. Upon processing and analyzing the two defocused images, the computer 162 provides separate, appropriate voltages to each of the wires attached to mirror M to cause appropriate deformations in the reflective surface of the deformable mirror M for correcting the aberrations in the eye E as measured by the wavefront sensor 150. As a result of such corrective deformation of the deformable mirror M, the image reaching the detector D' and displayed on video monitor 76 as the retina image Ir is corrected and the operator of the optical apparatus 110 may visually confirm that the corrections are adequate and complete. Again, as with the optical apparatus 10 illustrated in FIG. 2 and described above, the data developed by the wavefront sensor 150 and processed by computer 162 may be used for creating corrective spectacles, contact lenses, innerocular lenses, or performing corrective eye surgery. The results thereof may be checked on the apparatus 110 by again testing the eye E with the corrective lens or procedure in place and the deformable mirror M repositioned to a flat condition, whereupon the retina image Ir should be as optically perfect as possible and the wavefront sensor 150 with computer 162 should indicate that no other correction is required. If the corrected vision is not essentially perfect or of the level desired, such remaining imperfections will be observed on the monitor 76 and recorded by the wavefront sensor 150 and analyzed by the computer 162, whereby further corrections may be made.

Figure 5:
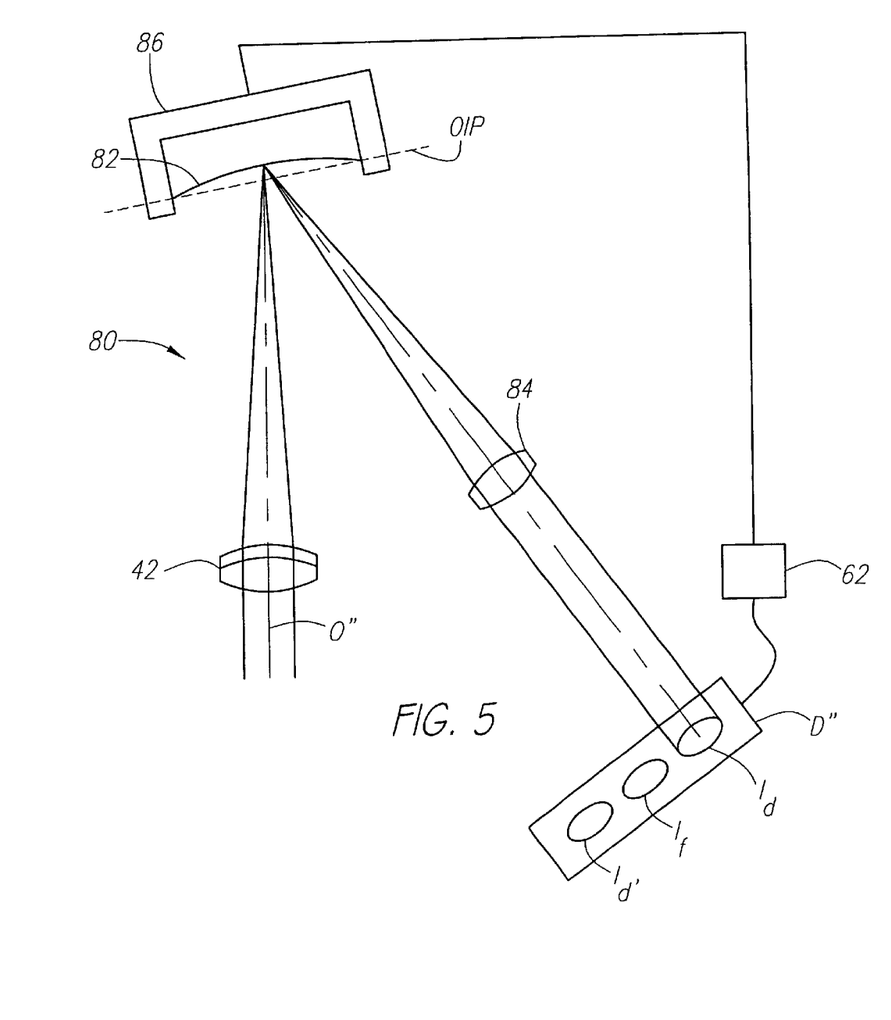
FIG. 5 is a diagrammatic plan view of an alternate form of wavefront curvature sensor for use in the apparatus of FIG. 2 or FIG. 4.

Referring now to FIG. 5, an alternative form of wavefront sensor is illustrated for further demonstrating that the method and apparatus of the present invention is not limited to the specific form of wavefront sensor shown in FIG. 2 and described with respect thereto. As with the embodiment of FIG. 2, the light reflected from the retina R of eye E proceeds along optical axis O through polarized beam splitter 34 (which items are not shown in FIG. 5) to and through the lens 42 on optical axis 0". The light beam is focused by lens 42 on an optical image plane OIP at a location slightly off-center of a flexible membrane mirror 82 from which the pupil image is reflected to and through a collimating lens 84 to an image detector D". When the flexible membrane mirror 82 is maintained in a flat condition, the pupil image If formed on the detector D" is focused. The flexible membrane mirror 82 and actuator (not shown) may be any device that is capable of being switched between positive and negative optical power, preferably by rapid switching, and examples of such devices are a piezo-electric bimorph mirror and an acoustically driven pellicle mirror. In any event, the mirror mount 86 is provided with means for causing flexing of the membrane mirror 82, which means may comprise acoustical, hydraulic, electrical, magnetic or other forms of actuators that will create a change in the curvature of the face of the mirror 82 from flat to either concave (as shown) or convex. By creating a curvature in the face of mirror 82, the pupil image Ip on detector D" becomes defocused. By selecting two equally and oppositely defocused images Id and Id' to be recorded by the computer 62, the wavefront curvature can be processed and analyzed in the same manner as described above with respect to the embodiment of FIG. 2. Preferably, the defocused images are equally defocused positively and negatively by deforming the membrane mirror 82 convexly and concavely, respectively, in the same amount, which is controlled by the computer 62, with the images being integrated over precisely equal (but opposite) flexing of the mirror. By decentering the image focused on the mirror 82, the focused image If appears in the center and the two defocused images appear on opposite sides thereof. For this embodiment of a wavefront sensor, the detector D" may use a CCD detector but for speed of operation, a more coarsely spatially-sampled detector may be used, such as a discrete array of PIN diodes or a customized small format CCD.

In the wavefront sensor 80 of FIG. 5, if the light beam is not reflected from the center of the flexible membrane mirror 82, some time dependent tilt is introduced when the membrane vibrates. If this is combined with a strobing light source synchronized with the membrane, several images can be recorded on a single detector with out blurring. If the light source is turned on very briefly when the membrane is concave, then flat and then convex, three images (as shown) will appear on the detector D" after one cycle of the membrane. Several cycles may be used for increasing the intensity of the images. Optically the membrane is similar to the wavefront sensor 50 where the membrane takes the place of the analyzer lens 56 and 58. This effect may be used in the case where the flexible mirror is an acoustically driven membrane whereby the two separate defocused images and potentially in-focus images may be recorded on a single imaging device whose frame rate is much slower than the membrane vibration frequency. Also, any method of sequentially tilting the wavefront mirror to the image on the membrane mirror would also serve to separate the defocused images on the detector D", such as by using an adaptive optics mirror like deformable mirror M shown in FIG. 4.

From the foregoing description of preferred embodiments and alternatives of the present invention of an optical apparatus for measuring the optical aberrations of the human eye, it will readily appear to those skilled in the art that various other embodiments, modifications and alternatives may be used without departing from the present invention as claimed below.

What is claimed:

1. An apparatus for measuring optical aberrations of the human eye, comprising;
   a light source for directing a predetermined light beam along the optical axis into the eye and onto the retina of the eye,
   a lens on the optical axis for reimaging the light from the eye retina of the light from the light beam,
   a wavefront curvature sensor for receiving the reimaged light and having means for forming two oppositely defocused pupil images on an image detector, and
   computer means for processing and analyzing the two defocused images for measuring the optical aberrations of the eye.

2. The apparatus of claim 1, wherein said wavefront curvature sensor means forming the two oppositely defocused pupil images forms one negatively defocused pupil image and one positively defocused pupil image of equal focus distances from an optical image plane.

3. The apparatus of claim 1, wherein said means for forming two oppositely defocused pupil images comprises a negatively powered lens forming one defocused pupil image and a positively powered lens forming the other defocused pupil image, said negatively powered lens and positively powered lens having equal focal lengths.

4. The apparatus of claim 1, wherein said means for forming two oppositely defocused pupil images comprises a flexible mirror positioned in the path of the reimaged light and means for causing the flexible mirror to flex to concave and convex conditions to reflect the pupil image to said image detector.

5. The apparatus of claim 4, wherein said flexible mirror is decentered with respect to the reimaged light for forming separate defocused images on said image detector.

6. The apparatus of claim 1, wherein the apparatus is provided with means for supporting the head and positioning the eye on the optical axis.

7. The apparatus of claim 1, wherein the apparatus provided with an illuminated target on the optical axis that is visible to the eye.

8. The apparatus of claim 1, wherein the apparatus is provided with a camera for recording a focused pupil image.

9. The apparatus of claim 1, wherein said light source emits a light beam that is substantially invisible to the human eye.

10. The apparatus of claim 9, wherein said light beam is polarized.

11. The apparatus of claim 1, wherein said light source is a laser diode.

12. The apparatus of claim 1, wherein a polarized beam splitter is provided on the optical axis for reflecting the light beam into the eye and allowing the light reflect from the retina to pass to said lens for reimaging that light.

13. The apparatus of claim 1, further comprising
    an illuminated target on the optical axis and visible by the eye for allowing the eye to focus on said target and for establish a position of the eye, and
    a collimating lens on the optical axis between the eye and said target, said collimating lens being movable along the optical axis for adjusting the apparent optical distance between the eye and said target.

14. The apparatus of claim 13, wherein said wavefront curvature sensor means forming the two oppositely defocused pupil images forms one negatively defocused pupil image and one positively defocused pupil image of equal focus distances from an optical image plane.

15. The apparatus of claim 13, wherein the apparatus s provided with means for supporting the head and positioning the eye on the optical axis.

16. The apparatus of claim 13, wherein the apparatus is provided with a camera for recording a focus pupil image.

17. The apparatus of claim 13, wherein said light source emits a light beam that is substantially invisible to the human eye.

18. The apparatus of claim 13, wherein a polarized beam splitter is provided on the optical axis for reflecting the light beam into the eye and allowing the light reflect from the retina to pass to said lens for reimaging that light.

19. The apparatus of claim 1, wherein said predetermined light beam is an annular ring.

20. the apparatus of claim 1, further including a mask in the path of the light source and having a central obscuration for eliminating light from the center of said predetermined light beam.

21. The apparatus of claim 20, wherein said central obscuration is of a size to prevent light reflected from optical surfaces of the eye from reaching said wavefront sensor.

22. The apparatus of claim 1, further comprising a deformable mirror positioned on the optical axis for receiving the reimaged light reflected from the retina, and means for causing controlled deformation of said mirror for correcting the measured aberrations.

23. The apparatus of claim 1 including a wavefront curvature sensor and adaptive optics means for correcting the sensed wavefront curvature produced by the eye.

24. The apparatus of claim 23, further comprising a deformable curvature mirror positioned on the optical axis for receiving the reimaged light reflected from the retina, and means for causing controlled deformation of said mirror for correcting the measured aberrations.

25. A method of measuring optical aberrations of the human eye, comprising the steps of;
    introducing a beam of light into the eye along an optical axis for forming a spot of light on the retina of the eye from which scattered light rays progress in a direction generally along the optical axis, reimaging the light scattered from the eye retina, optically producing two oppositely defocused pupil images on an image detector, and processing and analyzing the two defocused images for measuring the optical aberrations of the eye.

26. The method of claim 25, further comprising the step of establishing a position, at least momentarily, of the eye on an optical axis for eye-viewing along the optical axis before introducing the beam of light into the eye.

27. The method of claim 25, further comprising the step of providing an illuminated target visible to the eye along the optical axis for allowing the eye to focus on the target and remain substantially stationary during testing.

28. The method of claim 27 further including the step of recording a focused image of the pupil image substantially simultaneously with detecting the two defocused pupil images.

29. The method of claim 25, further including the step of recording a focused image of the pupil image substantially simultaneously with detecting the two defocused pupil images.

30. The method of claim 25, wherein the step of optically producing two oppositely defocused pupil images produces equal negatively and positively defocused images.

31. The method of claim 25, wherein the wavefront curvature is analyzed from the two oppositely defocused pupil images.

32. The method of claim 25, further including the step of directing the light scattered from the retina onto the surface of a deformable mirror and deforming said mirror based on the measured optical aberrations of the eye for correcting those aberrations.

33. The method of claim 25, wherein said light beam introduced into the eye is formed into an annular ring for inhibiting the reflection of light from the optical surfaces of the eye.

34. The method of claim 25, wherein said light beam introduced into the eye is strobed.

* * * * *